US009392788B2

(12) United States Patent
Ponnusamy et al.

(10) Patent No.: US 9,392,788 B2
(45) Date of Patent: Jul. 19, 2016

(54) MOSQUITO ATTRACTANT COMPOSITIONS AND METHODS

(75) Inventors: Loganathan Ponnusamy, Raleigh, NC (US); Ning Xu, Saskatoon (CA); Coby Schal, Cary, NC (US); Charles S. Apperson, Raleigh, NC (US); Dawn Wesson, New Orleans, LA (US)

(73) Assignee: North Carolina State University, Raleigh, NC (US)

( * ) Notice: Subject to any disclaimer, the term of this patent is extended or adjusted under 35 U.S.C. 154(b) by 891 days.

(21) Appl. No.: 12/613,920

(22) Filed: Nov. 6, 2009

(65) Prior Publication Data

US 2010/0192451 A1  Aug. 5, 2010

Related U.S. Application Data

(60) Provisional application No. 61/112,304, filed on Nov. 7, 2008.

(51) Int. Cl.
*A01N 63/02* (2006.01)
*A01N 37/02* (2006.01)

(52) U.S. Cl.
CPC .............. *A01N 37/02* (2013.01); *A01N 63/02* (2013.01)

(58) Field of Classification Search
None
See application file for complete search history.

(56) References Cited

U.S. PATENT DOCUMENTS

| | | | |
|---|---|---|---|
| 2,396,012 A * | 3/1946 | Jones et al. | 514/558 |
| 3,997,999 A | 12/1976 | Evans | |
| 4,282,673 A | 8/1981 | Focks et al. | |
| 4,844,892 A | 7/1989 | Laurence et al. | |
| 5,109,022 A * | 4/1992 | Jeanne et al. | 514/552 |
| 5,334,640 A | 8/1994 | Desai et al. | |
| 5,705,270 A | 1/1998 | Soon-Shiong et al. | |
| 5,795,570 A | 8/1998 | Weber et al. | |
| 5,858,384 A * | 1/1999 | Levy | 424/406 |
| 5,858,746 A | 1/1999 | Hubbell et al. | |
| 6,248,321 B1 | 6/2001 | Winder et al. | |
| 6,425,202 B1* | 7/2002 | Lin et al. | 43/107 |
| 6,481,152 B1 | 11/2002 | Gray | |
| 6,593,299 B1 | 7/2003 | Bennett et al. | |
| 6,718,687 B2 | 4/2004 | Robison | |
| 6,783,964 B2 | 8/2004 | Opara | |
| 6,800,279 B2 | 10/2004 | Bernier et al. | |
| 7,117,632 B2 | 10/2006 | Lin | |
| 7,413,781 B2 | 8/2008 | Hubbell et al. | |
| 7,434,351 B2 | 10/2008 | Bette | |
| 2003/0194454 A1* | 10/2003 | Bessette et al. | 424/745 |
| 2006/0165743 A1* | 7/2006 | Milani et al. | 424/405 |
| 2009/0148399 A1* | 6/2009 | Bette | 424/84 |

FOREIGN PATENT DOCUMENTS

JP  62006672 A  *  1/1987
WO  WO 03103395 A1  *  12/2003
WO  WO 2006126235 A1  *  11/2006

OTHER PUBLICATIONS

Ponnusamy et al., Supporting Information, PNAS(1998) [retrieved on Mar. 9, 2012]. Retrieved from the Internet< URL: http://www.pnas.org/cgi/content/short/0802505105>.*
Poonam et al., Oviposition Attractancy of Bacterial Culture Filtrates—Response of Culex quinquefasciatus, Mem. Inst. Oswaldo Cruz, Rio de Janeiro (2002), vol. 97, No. 3, pp. 359-362.*
Priya et al., Int. Res. J. Pharma. (2013), vol. 4, No. 4, pp. 28-34.*
Goswani et al., Journal of Scientif & Innovative Research (2004), vol. 3, No. 1, pp. 112-121.*
Sivakumar et al., Asian Pacific Journal of Tropical Medicine (2011), pp. 706-710.*
STN online, file AQUASCI, Acc. No. 82:26237, Doc. No. ASFA1 1985 15-06285 (Hwang, Oviposition-modifiying substances for mosquitoes (1981), No. 3, 44 pp. NTIS Order No. AD-A 125 421/8; DAMD17-79-C-9026), Abstract.*
STN online, file Biosis, Acc. No. 2006:232918, Doc No. PREV200600227309 (Ganesan et al., Australian Journal of Entomology (2006), vol. 45, No. Part 1, pp. 75-80), Abstract.*
Bentley MD and Day JF. Chemical ecology and behavioral aspects of mosquito oviposition. Ann Rev Entomol, 1989; 34: 401-421.
Reiter P et al. Enhancement of the CDC ovitrap with hay infusions for daily monitoring of Aedes aegypti populations. Journal of the American Mosquito Control Association. 1991; 7(1): 52-55.
Allan SA and Kline DL, Evaluation of organic infusions and synthetic compounds mediating oviposition in Aedes albopictus and Aedes aegypti (Diptera: Culcidae). Journal of Chemical Ecology. 1995; 21(11): 1847-1860.
Trexler JD et al. Laboratory and field evaluations of oviposition responses of Aedes albopictus and Aedes triseriatus (Diptera: Culicidae) to oak leaf infusions. Journal of Medical Entomology. 1998; 35(6): 967-976.
Sant'ana AL et al. Characteristics of grass infusions as oviposition attractants to Aedes (Stegomyia) (Diptera: Culicidae). Journal of Medical Entomology. 2006; 43(2): 214-220.
Ponnusamy L et al. Identification of bacteria and bacteria-associated chemical cues that mediate oviposition site preferences by Aedes aegypti. PNAS. Jul. 8, 2008; 105(27): 9262-9267.
Benzon GL and Apperson CS. Reexamination of chemically mediated oviposition behavior in Aedes aegypti (L.) (Diptera: Culicidae). Journal of Medical Entomology. May 1988; 25(3): 158-164.
Barbosa et al. "Evaluation of an oviposition-stimulating kairomone for the yellow fever mosquito, *Aedes aegypti*, in Recife, Brazil" *Journal of Vector Ecology* 35(1):204-207 (2010).

* cited by examiner

*Primary Examiner* — Abigail Fisher
*Assistant Examiner* — Frank Choi
(74) *Attorney, Agent, or Firm* — Myers Bigel & Sibley, P.A.

(57) ABSTRACT

Provided are compositions for attracting and/or stimulating oviposition. The compositions comprise a suitable carrier and a bacterium capable of producing nonanoic acid, tetradecanoic acid, or methyl tetradecanoate; *Bacillus thuringiensis; Lactococcus lactis; Klebsiella oxytoca; Shigella dysenteriae; Brevundimonas vesicularis*; a supernatant of a culture of any of the these bacteria; nonanoic acid; tetradecanoic acid; or methyl tetradecanoate, or any combination thereof, at a concentration effective to attract the mosquito to a target. The compositions may be comprised within a kit or trap. Also provided are methods of attracting mosquitoes to a target.

22 Claims, 8 Drawing Sheets

MOSQUITO ATTRACTANT COMPOSITIONS AND METHODS

CROSS-REFERENCE TO RELATED APPLICATIONS

This application claims priority to U.S. Provisional Patent Application No. 61/112,304 filed on Nov. 7, 2008, the entire contents of which are incorporated herein by reference.

STATEMENT REGARDING FEDERALLY SPONSORED RESEARCH

This invention was made with government support under grant number U01-AI-58303-01 from the NIH, NIAD. The U.S. Government has certain rights to this invention.

FIELD OF THE INVENTION

The present invention concerns mosquito attractants and methods of using the same.

INTRODUCTION

Mosquitoes serve as vectors for the spread of several diseases that severely impact the health of humans, pets, and livestock. For example, the mosquito *Aedes aegypti* is the principal vector responsible for the spread of several viruses pathogenic to humans, including dengue and yellow fever viruses. Dengue fever is a major public health problem in tropical regions worldwide. The World Health Organization estimates that 51 million infections with the dengue fever occur annually and 2.5-3 billion people are at risk in the 100 countries where dengue fever occurs. There has been a dramatic rise in the number of cases of dengue hemorrhagic fever in Asia, and recently dengue fever has been introduced into Central and South America.

There is a continuing need in the art for compositions and methods for monitoring, affecting the behavior of, and/or controlling mosquito populations.

SUMMARY OF THE INVENTIONS

In one aspect, the invention provides a mosquito attractant composition comprising a suitable carrier and one or more of: a bacterium capable of producing nonanoic acid, tetradecanoic acid, or methyl tetradecanoate; *Bacillus thuringiensis; Lactococcus lactis; Klebsiella oxytoca; Shigella dysenteriae; Brevundimonas vesicularis*; a supernatant of a culture of any of the aforementioned bacteria; nonanoic acid; tetradecanoic acid; or methyl tetradecanoate, or any combination thereof.

In another aspect, the invention provides a method of attracting a mosquito to a target, the method comprising applying to the target a mosquito attractant comprising one or more of: a bacterium capable of producing nonanoic acid, tetradecanoic acid, or methyl tetradecanoate; *Bacillus thuringiensis; Lactococcus lactis; Klebsiella oxytoca; Shigella dysenteriae; Brevundimonas vesicularis*; a supernatant of a culture of any of the aforementioned bacteria; nonanoic acid; tetradecanoic acid; or methyl tetradecanoate, or any combination thereof in an amount effective to attract the mosquito to the target.

In another aspect, the invention provides a mosquito trap comprising a trapping chamber or adhesive, and a composition comprising a suitable carrier and one or more of: a bacterium capable of producing nonanoic acid, tetradecanoic acid, or methyl tetradecanoate; *Bacillus thuringiensis; Lactococcus lactis; Klebsiella oxytoca; Shigella dysenteriae; Brevundimonas vesicularis*; a supernatant of a culture of any of the aforementioned bacteria; nonanoic acid; tetradecanoic acid; or methyl tetradecanoate, or any combination thereof, the composition positioned to attract the mosquito.

In yet another aspect, the invention provides a kit comprising a composition as described above and a toxicant, classical attractant, or growth regulator.

DETAILED DESCRIPTION OF THE PREFERRED EMBODIMENTS

Figure 1:
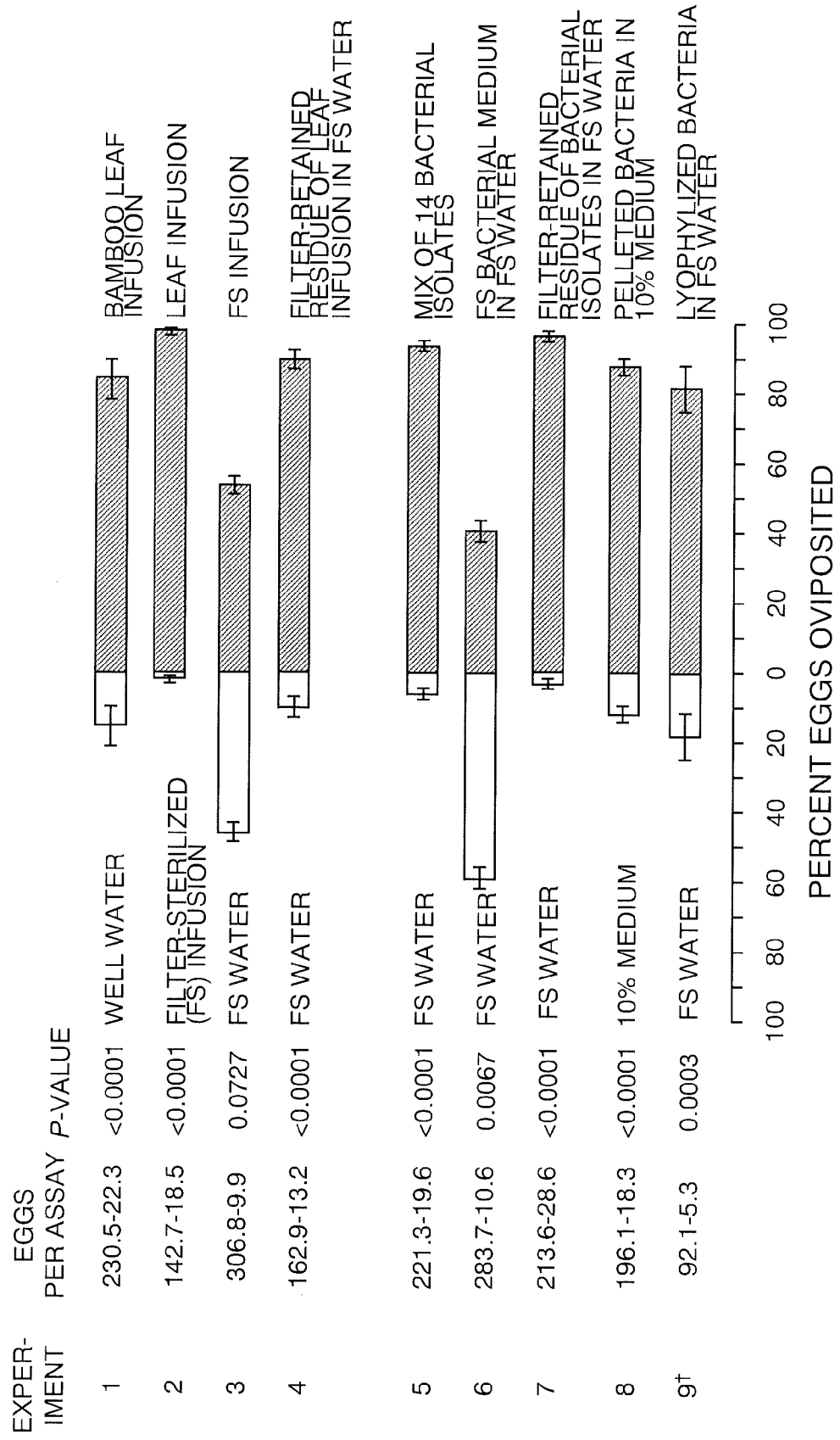
FIG. 1. Egg laying responses of *Ae. aegypti* to different bamboo leaf infusion and bacterial isolates cultured from the infusions, in 24 h oviposition assays.

Provided are compositions and methods for affecting the behavior of mosquitoes. Although referred to herein as mosquito "attractants," the compositions may or may not function as classical attractants, i.e., compositions that attract mosquitoes to a site. In fact, without being limited as to theory, it is believed that, in some embodiments, the compositions may serve as arrestants that cause mosquitoes to stay at a site longer and/or as stimulants that cause mosquitoes to oviposition, i.e., lay eggs, or to lay more eggs at a single site.

As described in detail in the Examples, it was discovered that certain bacterial species and compounds produced by the bacteria can serve as mosquito attractants. Certain of the compounds have been further characterized and/or identified.

"Mosquito" as used herein encompasses any type of mosquito (e.g., *Anopheles, Aedes, Ochlerotatus,* and *Culex*), including but not limited to Tiger mosquitoes, *Aedes aborigines, Aedes Aegypti, Aedes albopictus, Aedes cantator, Aedes sierrensis, Aedes sollicitans, Aedes squamigeer, Aedes stictiucs, Aedes vexans, Anopheles quadrimaculatus, Culex pipiens, Culex quinquefaxciatus,* and *Ochlerotatus triseriatus.*

The compositions comprise a suitable carrier and an attractant bacteria, bacterial culture supernatant thereof, or attractant compound. A bacterial culture supernatant may include a bacterial cell extract or filtered bacterial culture. Attractant activity may be determined as described in the Examples. Optionally, the attractant compound may be comprised within the bacterial culture supernatant. In some embodiments, the bacteria may be isolated bacteria.

The bacteria may include *Bacillus thuringiensis, Enterobacter asburiae, Enterobacter cancerogenus, Pseudomonas fulva, Pseudomonas putida, Lactococcus lactis, Enterobacter gergoviae, Enterobacter ludwigii, Klebsiella oxytoca, Klebsiella granulomatis, Pseudomonas plecoglossicida, Rhizobium huautlense, Shigella dysenteriae, Citrobacter freundii, Brevundimonas vesicularis, Porphyrobacter sp., Variovorax koreensis, Agrobacterium tumefaciens, Rhizobium huautlense, Acidiphilium rubrum, Acidovorax avenae, Pseudomonas lanceolata, Variovorax koreensis, Klebsiella granulomatis, Pseudomonas syringae, Curvibacter gracilis, Caulobacter fusiformis, Sphingomonas aromaticivorans, Escherichia hermannii, Pantoea agglomerans, Klebsiella pneumoniae, Agrobacterium rubi, Brevibacillus brevis, Bacillus thuringiensis, Baccillys sp., Lactococcus lactis, Enterobacteraceae sp., Enterobacter sp., Pseudomonas, Roseomonas, Sphingomonas, Porphyrobacter, Sphingobium, Acidovorax, Variovorax sp., Hydrogenophaga sp., Flavobacterium sp.,* and *Azorhizobium caulinodans,* or a bacterial culture supernatant thereof.

In some embodiments, a bacteria may include any bacterium having the characteristics of the bacterial isolates described herein, or they may include the specific isolates. Bacterial isolates according to the invention may be isolated as described in Examples 1-5. For example, effective bacterial isolates may include, but are not limited to, isolates B1 through B14 and WO1 through WO18 (Table 1).

In some embodiments, the composition comprises *Bacillus thuringiensis* or a bacterial culture supernatant thereof. In some embodiments, the composition comprises *Lactococcus lactis* or a bacterial culture supernatant thereof. In some embodiments, the composition comprises *Klebsiella oxytoca* or a bacterial culture supernatant thereof. In some embodiments, the composition comprises *Shigella dysenteriae* or a bacterial culture supernatant thereof. In some embodiments, the composition comprises *Brevundimonas vesicularis* or a bacterial culture supernatant thereof. It is envisioned that any isolate of *Bacillus thuringiensis, Lactococcus lactis, Klebsiella oxytoca, Shigella dysenteriae,* or *Brevundimonas vesicularis* may be used in the compositions and methods of the invention, provided the isolate has the ability to serve as a mosquito attractant.

The compositions may include a single bacterial species (e.g., any one of *Bacillus thuringiensis, Lactococcus lactis, Klebsiella oxytoca, Shigella dysenteriae,* or *Brevundimonas vesicularis*), or a plurality of these bacterial species (e.g., two, three, four, or five or more species), in any of the possible combinations. The compositions may comprise the plurality of bacterial species as a blend.

When bacterial supernatants are used, they can be unpurified supernatants or purified or partially purified supernatants. When the supernatants are purified or partially purified, they preferably contain active fractions (e.g., bacteria-associated carboxylic acids and/or methyl esters that function as attractants and/or stimulate oviposition).

These and other active compounds may be identified from bacteria, for example, as described in Example 13. Active compounds can be produced by any suitable means (e.g., produced by bacterial fermentation, synthesized, or purchased from a source).

In some embodiments, the compositions may comprise at least one compound. The at least one compound may be selected from carboxylic acids and esters. For example, compounds may include, but are not limited to, nonanoic acid, decanoic acid, dodecanoic acid, tetradecanoic acid, tetradecanoic acid methyl ester, hexadecanoic acid, hexadecanoic acid methyl ester, or octadecanoic acid, or a combination thereof. Suitably, the at least one compound may be selected from nonanoic acid, tetradecanoic acid, and methyl tetradecanoate, and any combination of two or three thereof.

The composition may comprise a blend of compounds. When more than one compound is used, the compounds may be present in effective ratios. For example, the compounds may be present in a ratio similar to that found in nature, as described in Example 13. For example, the composition may comprise a blend of nonanoic acid, tetradecanoic acid, and methyl tetradecanoic acid in a weight ratio of about 16:83:1, respectively. As one of skill in the art will appreciate, the compositions may also include other ratios of nonanoic acid, tetradecanoic acid, and methyl tetradecanoic acid. Using more than one compound may extend the range of effective dosages and/or may reduce the amount of total attractant or of a specific attractant effective to attract mosquitoes, arrest mosquitoes, or stimulate ovipositioning, or a combination thereof.

The composition may be provided in a concentrated form (i.e., in a form that requires dilution prior to use or which is diluted upon delivery to the site of use) or in a dilute form that is suitable for use in the methods without dilution.

The methods employ an effective amount of at least one bacteria, bacterial supernatant thereof, or compound, or combination thereof. As used herein, "effective amount" is an amount effective to increase the number of mosquitoes at a target, and/or to increase the number of mosquito eggs laid at a target, relative to a control. Suitable controls include similar untreated sites, mock treated sites, e.g., sites treated with water or a carrier that does not contain a mosquito attractant.

The Examples describe how one would go about determining the dose-response of ovipositioning by particular species of mosquitoes as a function of bacterial cell concentration. Thus, using the teachings provided herein, it is well within the ability of one skilled in the art to determine an effective concentration of bacterial cells for use in the methods of the invention.

For example, the methods of the invention, which optionally may be carried out using the compositions of the invention, may employ final concentrations of at least about 1 ng, at least about 10 ng, at least about 100 ng, at least about 0.001 mg, at least about 0.01 mg, or at least about 0.1 mg with respect to a single compound or the total of two or more compounds. The composition may comprise less than about 1 mg, less than about 0.1 mg, less than about 0.01 mg, less than about 0.001 mg, less than about 100 ng, or less than about 10 ng of total compound. The methods may employ compounds in a concentration of from about 1 ng to about 100 ng of total compound. The methods may employ final concentrations of compound at the target of at least about 0.03 ng/mL, at least about 0.3 ng/mL, at least about 3.0 ng/mL, or at least about 30 ng/mL. The methods may employ compound in a final concentration of at the target of less than about 300 ng/mL, less than about 30 ng/mL, or less than about 3.0 ng/mL. The methods may employ compound such that the final concentration of compound at the target is about 0.03 to about 3.33 ng/mL.

In some embodiments, the compositions may comprise at least one compound and at least one bacteria, as defined above.

The composition may comprise an effective amount of at least one bacteria, bacterial supernatant thereof, or compound, or combination thereof.

In some embodiments, the compositions may comprise or the methods may employ, in a formulation separate from the composition, an additional component including, but not limited to, a classical attractant, a toxicant, or mosquito growth regulators (e.g., growth inhibitors). It is specifically envisioned that growth regulators can be horizontally transferred to mosquito eggs or larvae at other locales, e.g., by transfer to adjacent water containers through skip-oviposition.

Toxicants may include, but are not limited to, larvacides, adulticides, and pesticides such as DDT. Additional components may include, but are not limited to, pesticides, insecticides, herbicides, fungicides, nematicides, acaricides, bactericides, rodenticides, miticides, algicides, germicides, repellents, nutrients, and combinations thereof. Specific examples of insecticides include, but are not limited to, a botanical, a carbamate, a microbial, a dithiocarbamate, an imidazolinone, an organophosphate, an organochlorine, a benzoylurea, an oxadiazine, a spinosyn, a triazine, a carboxamide, a tetronic acid derivative, a triazolinone, a neonicotinoid, a pyrethroid, a pyrethrin, and a combination thereof. Specific examples of herbicides include, without limitation, a urea, a sulfonyl urea, a phenylurea, a pyrazole, a dinitroaniline, a benzoic acid, an amide, a diphenylether, an imidazole, an aminotriazole, a pyridazine, an amide, a sulfonamide, a uracil, a benzothiadiazinone, a phenol, and a combination thereof. Specific examples of fungicides include, without limitation, a dithiocarbamate, a phenylamide, a benzimidazole, a substituted benzene, a strobilurin, a carboxamide, a hydroxypyrimidine, a anilopyrimidine, a phenylpyrrole, a sterol demethylation inhibitor, a triazole, and a combination thereof. Specific examples of acaricides or miticides include, without limitation, rosemary oil, thymol, spirodiclogen, cyflumetofen, pyridaben, diafenthiuron, etoxazole, spirodiclofen, acequinocyl, bifenazate, and a combination thereof.

The compositions of the invention may comprise the attractant bacteria or compounds encapsulated within, deposited on, or dissolved in a carrier. As used herein, a carrier may comprise a solid, liquid, or gas, or combination thereof. Suitable carriers are known by those of skill in the art. For example, liquid carriers may include, but are not limited to, water, media, glycerol, or other solution. The attractant composition may be in any suitable form, including but not limited to liquid, gas, or solid forms or shapes known in the art such as pellets, particles, beads, tablets, sticks, pucks, briquettes, pellets, beads, spheres, granules, micro-granules, extrudates, cylinders, ingot, and the like. In some embodiments, the composition may be provided in a quick-release composition, an extended release composition, or a combination thereof.

Suitable carriers may include, but are not limited to, biodegradable polymers, talcs, attapulgites, diatomites, fullers earth, montmorillonites, vermiculites, synthetics (such as Hi-Sil or Cab-O-Sil), aluminum silicates, apatites, bentonites, limestones, calcium sulfate, kaolinities, micas, perlites, pyrophyllites, silica, tripolites, and botanicals (such as corn cob grits or soybean flour), and variations thereof that will be apparent to those skilled in the art The solid support or carrier can be a macromer, including, but not limited to, ethylenically unsaturated derivatives of poly(ethylene oxide) (PEG) (e.g., PEG tetraacrylate), polyethylene glycol (PEG), polyvinyl alcohol (PVA), poly(vinylpyrrolidone) (PVP), poly(ethyloxazoline) (PEOX), poly (amino acids), polysaccharides, proteins, and combinations thereof. Carriers may also include plaster. Carriers may also include fluids such as medium or water.

Polysaccharide solid supports include, but are not limited to, alginate, hyaluronic acid, chondroitin sulfate, dextran, dextran sulfate, heparin, heparin sulfate, heparin sulfate, chitosan, gellan gum, xanthan gum, guar gum, water soluble cellulose derivatives, carrageenan, and combinations thereof.

Protein solid supports include, but are not limited to, gelatin, collagen, albumin, and combinations thereof.

In some embodiments, live cultures of the one or more bacteria are mixed with a macromer solution (e.g. a polysaccharide salt such as sodium alginate) and the macromer solution deposited as drops or droplets into a (preferably sterile) salt solution (e.g., $CaCl_2$) to form beads.

Attractant compositions can be produced from cultures of attractant bacteria by any suitable means. A variety of techniques are known for suspending or combining live cells with solid supports, including, but not limited to, those described in U.S. Pat. Nos. 7,413,781; 6,783,964; 6,248,321; 5,858, 746; 5,795,570; 5,705,270; 5,334,640; and variations thereof that will be apparent to those skilled in the art.

Where compounds or supernatants/fermentation products are utilized rather than cells, the compounds can be combined with any suitable support, including but not limited to biodegradable polymers, talcs, powders, etc., as is also known in the art, as described in U.S. Pat. Nos. 7,117,632; 6,800,279; 6,593,299; 4,844,892; and variations thereof that will be apparent to those skilled in the art.

In other embodiments, the invention provides methods of attracting at least one mosquito to a target. The invention also provides methods of stimulating at least one mosquito to oviposition, i.e., lay eggs. In some embodiments, the invention provides methods of attracting at least one mosquito and stimulating the mosquito to oviposition. The methods may comprise applying a composition comprising at least one bacteria, a bacterial supernatant thereof, at least one compound, or a combination thereof, as described above, to the target. As used herein, "target" is a surface, site, or container known in the art. A container may contain a fluid such as water.

The methods of the invention may be carried out by applying attractant bacteria, supernatants, compounds, or compositions as described herein to a target article or site to which mosquitoes are to be attracted. In some embodiments, the applying step is carried out by applying the bacterial culture supernatant, optionally in sterile form, or utilizing attractant compounds as described herein. In some embodiments, the mosquitoes are *Aedes* mosquitoes (e.g., *Aedes aegypti* or *Aedes albopictus*). In some embodiments, the mosquitoes are gravid.

The methods and compositions can be implemented as a mosquito trap. Such a trap may include (i) a trapping chamber or adhesive and (ii) an attractant positioned to attract mosquitoes to the trapping chamber or adhesive, wherein an attractant as described herein is utilized as the attractant. Any suitable trap configuration can be used, including, but not limited to, those described in U.S. Pat. Nos. 7,434,351; 6,718, 687; 6,481,152; 4,282,673; 3,997,999; and variations thereof that will be apparent to those skilled in the art.

Without being limited to theory, it is thought that the final decision by a gravid female such as *Ae. aegypti* to accept or reject an oviposition site might involve a two-step process: First, upon alighting on water within a container, she may determine the presence and measure the relative concentration of various bacteria and associated semiochemicals (which are likely structural components of the bacterial cell wall) using contact chemoreceptors, most likely on her antennae, mouthparts, tarsi, or ovipositor. She may thus obtain information about the composition and density of the microbial community in the water container. The female may also obtain mechanosensory information from microbes and whether she engages in behaviors that facilitate the flux of bacteria across mechano- and chemosensilla. In a second step, the female may integrate sensory information from chemostimulatory and chemodeterrent cues, together with other chemical (e.g., pH, alkalinity) and mechanical cues, to resolve whether the water container represents a suitable oviposition site. There may be strong selection pressure on gravid females for accurate egg-laying decisions because the microbial community within the oviposition container must support growth and development of her offspring, which graze on microbes. Thus, the concentration and relative amounts of keystone fatty acids and esters might represent to the female a suitable microbial community at an acceptable cell density. Conversely, the presence of deterrent compounds or even stimulatory fatty acids at high concentrations, may represent to the *Ae. aegypti* female a more eutrophic container community that is less suitable for her larvae.

Furthermore, a pivotal life-history trait of *Ae. aegypti* is skip oviposition, where gravid females disperse single eggs or small groups of eggs into multiple water containers. That is, each oviposition bout is punctuated by appetitive flight seeking another oviposition site. The oviposition-stimulating bacteria and compounds might (i) bias females' decisions in favor of oviposition over flight and (ii) cause a quantitative shift from egg retention to oviposition. Both effects may result in longer contact with the water surface and possibly the inner container walls. Of several practical implications, two may have farreaching effects on mosquito populations and hence on the epidemiology of vectored diseases. First, increasing the numbers of eggs laid in target containers would likely enhance the sensitivity of oviposition traps that are used to detect and monitor the activity of *Ae. aegypti* in disease-endemic regions. Second, increasing the residence time within containers would assure that females receive ample exposure to traps impregnated with lethal toxicants or with biologically active materials, such as insect growth regulators, that can be horizontally transferred to adjacent water containers through skip-oviposition. In addition to their potential in mosquito management programs, the oviposition-inducing semiochemicals may facilitate investigations of contact-mediated chemoreception in a mosquito vector of substantial public health importance globally.

It is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application. All U.S. patents cited herein are incorporated by reference herein in their entirety. The present invention is explained in greater detail in the Examples set forth below.

EXAMPLES

Example 1

Origin of Mosquito and Bacterial Isolates

*Aedes aegypti* and *Ae. albopictus* colonies were established from field-collected eggs from New Orleans, La. in 2003. Larvae of both mosquito species were reared and maintained as described by Trexler et al. (1998) at ~28° C. and ~75% relative humidity, and a photoperiod of 14 h light/10 h of dark, including two twilight periods of 60 min each. Mosquitoes were blood-fed on a human forearm, 4-5 days prior to set up of each experiment. Plant infusions were prepared by fermenting 33.6 g of senescent bamboo leaves in 4 L of well water in separate Teflon bags. Bamboo leaves were obtained from a residential area in Raleigh, N.C.

Example 2

Preparation of Plant Infusions

Plant infusions were prepared by fermenting 16.8 g of white oak or 33.6 g of bamboo senescent leaves in 4 liters of well water in separate Teflon bags. Bamboo and white-oak leaves were obtained from separate residential areas in Raleigh, N.C. 1-week-old bamboo and 2-week-old white-oak leaf infusion were found to be attractive to *Aedes* mosquitoes in behavioral bioassays. Before use in bioassays, whether they were filtered or not, infusions were diluted 1:1 with well water.

Example 3

Bioassay Methods

Modifications of the olfactory- and contact-mediated bioassays previously described (Trexler J D, Apperson C S, Schal C (1998) J Med Entomol 35:967-976) were used to measure the response of gravid mosquitoes to plant infusions (or bacterial compounds). Briefly, two 125-mL polypropylene cups (test and control) were placed randomly in diagonal corners of a Plexiglas cage (30×30×30 cm) that was fitted with a stockinet cloth sleeve (AlbaHealth, Rockwood, Tenn.). Each cup was filled with 30 mL of either test or control solution. White paper sleeves were placed around each bioassay cup to mask visual cues presented by darkly colored leaf infusions. Adults had ad libitum access to water contained in a polypropylene cup that was fitted with a lid with a cotton wick protruding through a hole in the lid. For egg-laying bioassays, either one or five gravid females were released in each replicate cage. Cages were placed randomly on racks in a room where environmental conditions were the same as in the insectary. After a 24 h exposure period, eggs laid on the surface of the water in the test and control cups were counted. In olfactory bioassays, 10 gravid females were released in each bioassay cage. A circular metal wire-mesh screen covered with insect glue (Tanglefoot; Tanglefoot Co.) was inserted in each cup on top of an insert cut from a 120-mL polypropylene cup. Sticky screens were placed above test and control media, 2.5 cm below the lip of each cup. The mesh size of the metal screen prevented females from entering without landing on the screen. Therefore, positive or negative responses to the test infusions were measured by the numbers of females trapped during a 24 h exposure period on the sticky screen in the test and control cups.

Statistical Analysis

For each replicate bioassay cage, the numbers of eggs laid in the test and control cups were converted to the proportion of the total number of eggs laid. The proportions were subjected to an arcsin $\sqrt{x}$ transformation to achieve approximate normality. A one-tailed paired t test was used to determine whether differences in the mean transformed proportion of eggs deposited in test and control cups were statistically significant.

Example 4

Behavioral Bioassay—Response to Odorants from Plant Infusions

Using binary choice behavioral assays as described in Example 3, we screened bamboo (*Arundinaria gigantea*) leaf infusions and found that *Ae. aegypti* females directed 84.3±5.6% (SEM) of their eggs to 1-week-old infusions (Example 2), and only a small fraction of the eggs were laid in control containers holding water (t=5.697, df=11, P<0.0001) (FIG. 1, experiment 1). To evaluate the role of microorganisms in egg laying, gravid *Ae. aegypti* females were offered a choice of a bamboo infusion and an identical infusion that had been filtered through a 0.22-μm filter to remove microorganisms. Significantly more eggs were laid in bioassay cups containing the unfiltered infusion than in cups holding filter-sterilized infusion (FIG. 1, experiment 2). Because some organic infusions contain odorants that can attract gravid females, egg laying was compared in filter-sterilized infusions, which remained attractive to mosquitoes and, filter-sterilized water, which was comparatively less attractive. No significant difference was found in the number of eggs deposited in these containers (FIG. 1, experiment 3), indicating that filtration removed the oviposition cues and, therefore, that these cues likely were not solubilized in the infusion, but rather associated with the filtered microbes. The attractiveness of filter-sterilized infusion was also compared to sterile water (same procedure as in experiment 3), using the olfactory bioassay. Importantly, the filter-sterilized bamboo leaf infusions did not lose their attractiveness to mosquitoes: The sticky screen positioned just above the infusion surface trapped 5.6±0.5 (77.4%) of 10 females in the infusion cup and only 1.8±0.5 females in the control water cup (t=4.171, df=11, P<0.0001). By comparing the attractiveness of an unfiltered bamboo-leaf infusion and a filter-sterilized infusion, it was confirmed that oviposition attractants, unlike oviposition stimulants, were dissolved in the organic infusion and could not be removed solely by filtering the microorganisms (52.0±4.5% vs. 48.0%, respectively, t=0.411, df=11, P=0.3443).

Figure 2:
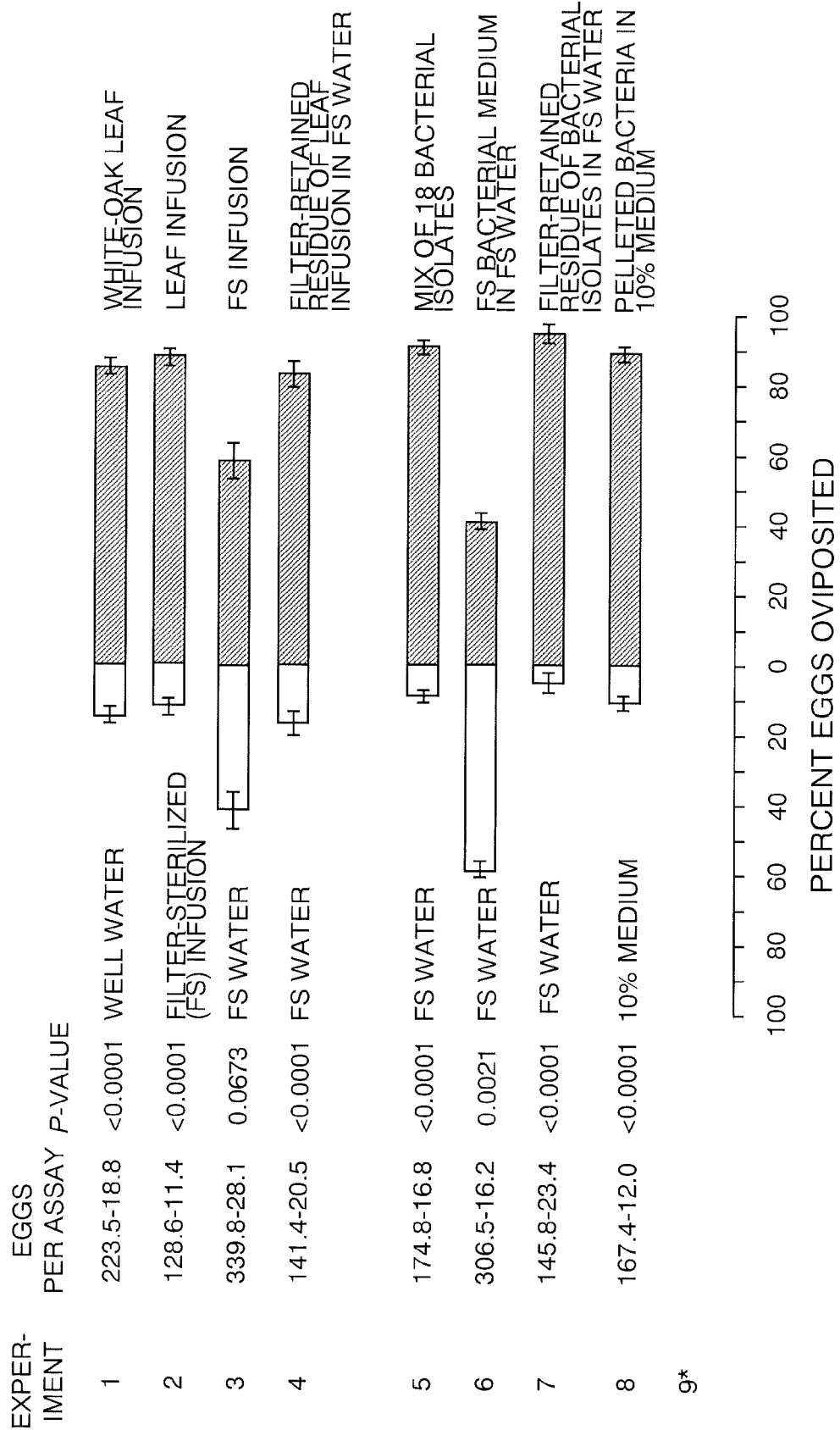
FIG. 2. Egg laying responses of *Ae. aegypti* to different white oak leaf infusion and bacterial isolates cultured from the infusions, in 24 h oviposition assays.

Next, a replacement experiment was conducted to confirm that microorganisms mediated oviposition decisions. Bamboo-leaf infusions were consecutively filter-sterilized using two freshfilter membranes, and the filtered microorganisms were resuspended in sterile water that had been filtered once. *Ae. aegypti* laid significantly more eggs in filter-sterilized water augmented with the first filter membrane (with microorganisms) than in sterilized infusion with the contents of the second filter membrane (FIG. 1, experiment 4). Taken together, the results of these behavioral assays indicate that cues associated with microorganisms in plant infusions direct gravid *Ae. aegypti* females to deposit >90% of their eggs in microbe-enriched containers. Although microorganisms also produce volatile metabolites that attract gravid females to infusions, these odorants do not induce egg-laying. Similar results were obtained in an identical set of experiments conducted with white-oak (*Quercus alba*) leaf infusions (FIG. 2, experiments 1-3), indicating that the cues that mediate oviposition decisions in female *Ae. aegypti* are not unique to bamboo-leaf infusions.

Example 5

Purification and Identification of Bacterial Isolates

Bacterial cells from bamboo leaf infusions were cultured in R2A medium. Bacteria were isolated from the culture medium, purified and identified as described above. Briefly, enrichment cultures were established by inoculating 1 mL each of undiluted 1- to 2-week old bamboo-leaf and white-oak leaf infusions into separate 250-mL flasks, each containing 100 mL of culture medium. Bacterial cultures were grown for 2 days at 28° C. with constant shaking (120 rpm). Enriched cultures were serially diluted to $10^{-7}$ with sterile peptone water 0.1% (wt/vol), and 100 μL of each of the last three dilutions was separately spread on two replicate R2A agar plates to isolate bacterial species, after which the plates were incubated at 28° C. Similarly, 1 mL of each plant infusion was also serially diluted up to $10^{-5}$ and spread-plated on R2A agar. Colonies with visually distinct morphologies were restreaked several times on R2A agar plates.

In total, 14 and 18 different bacterial isolates from bamboo-leaf and white-oak leaf infusions, respectively, were purified. Bacterial isolates from each plant infusion were mixed (14 isolates from bamboo-leaf infusions and 18 isolates from white-oak leaf infusions), and grown for 2-days in R2A medium, and the bacterial cells in these cultures were used in contact chemoreception bioassays.

As stated, in total, 14 different bacterial isolates from bamboo leaf infusion were purified, genomic DNA was isolated, 16S rRNA fragments were amplified by PCR, and the amplicons were sequenced to identify the bacterial isolates to species. All isolated could be assigned to recognized phyla of domain bacteria (Table 1). Similarity among the sequences was analyzed. Nine bamboo isolates and 8 white oak isolates had ≥98% sequence identity to described bacterial species, and 5 bamboo isolates and 10 white-oak isolates were considered previously unrecognized based on ≤97% match with described bacterial species. Particularly notable is the large number of members of the phylum *Proteobacteria* (affiliated with subdivisions alpha and gamma). On the basis of 16S rRNA gene sequence similarities, some of these isolates are members of bacterial taxa for which pure-culture isolates have not previously been obtained.

TABLE 1

Identification of bacterial species isolated from bamboo and white-oak leaf infusions.

| Isolate* | No. of bases used to establish identity | Accession Number in GenBank | Species corresponding to closest relative (% sequence identity) | Phylogenetic affiliation |
|---|---|---|---|---|
| B1 | 714 | EU341308 | *Bacillus thuringiensis* (99) | Firmicutes |
| B2 | 617 | EU341309 | *Enterobacter asburiae* (98) | Gammaproteobacteria |
| B3 | 760 | EU341310 | *Enterobacter cancerogenus* (98) | Gammaproteobacteria |
| B4 | 758 | EU341311 | *Pseudomonas fulva* (99) | Gammaproteobacteria |
| B5 | 763 | EU341312 | *Lactococcus lactis* (99) | Firmicutes |
| B6 | 743 | EU341313 | *Entobacter gergoviae* (97) | Gammaproteobacteria |
| B7 | 770 | EU341314 | *Enterobacter ludwigii* (97) | Gammaproteobacteria |
| B8 | 783 | EU341315 | *Klebsiella oxytoca* (98) | Gammaproteobacteria |
| B9 | 770 | EU341316 | *Klebsiella granulomatis* (98) | Gammaproteobacteria |
| B10 | 716 | EU341319 | *Pseudomonas plecoglossicida* (99) | Gammaproteobacteria |
| B11 | 770 | EU341318 | *Rhizobium huautlense* (97) | Alphaproteobacteria |

TABLE 1-continued

Identification of bacterial species isolated from bamboo and white-oak leaf infusions.

| Isolate* | No. of bases used to establish identity | Accession Number in GenBank | Species corresponding to closest relative (% sequence identity) | Phylogenetic affiliation |
|---|---|---|---|---|
| B12 | 604 | EU341319 | *Shigella dysenteriae* (76) | Gammaproteobacteria |
| B13 | 764 | EU341320 | *Citrobacter freundii* (97) | Gammaproteobacteria |
| B14 | 511 | EU341321 | *Brevundimonas vesicularis* (98) | Alphaproteobacteria |
| WO1 | 483 | EF685171 | *Porphyrobacter* sp. (97) | Alphaproteobacteria |
| WO2 | 400 | EF685175 | *Pseudomonas lanceolata* (98) | Betaproteobacteria |
| WO3 | 464 | EU489484 | *Variovorax koreensis* (97) | Betaproteobacteria |
| WO4 | 490 | EF685166 | *Agrobacterium tumefaciens* (99) | Alphaproteobacteria |
| WO5 | 328 | EF685177 | *Rhizobioum huautlense* (96) | Alphaproteobacteria |
| WO6 | 480 | EU489485 | *Enterobacter asburiae* (98) | Gammaproteobacteria |
| WO7 | 525 | EF685176 | *Acidiphilium rubrum* (89) | Alphaproteobacteria |
| WO8 | 356 | EF685167 | *Acidovorax avenae* (90) | Betaproteobacteria |
| WO9 | 480 | EF685170 | *Pseudomonas lanceolata* (97) | Betaproteobacteria |
| WO10 | 585 | EF685164 | *Variovorax koreensis* (90) | Betaproteobacteria |
| WO11 | 360 | EU489486 | *Klebsiella granulomatis* (99) | Gammaproteobacteria |
| WO12 | 529 | EF685178 | *Pseudomonas syringae* (98) | Gammaproteobacteria |
| WO13 | 400 | EF685175 | *Curvibacter gracilis* (97) | Betaproteobacteria |
| WO14 | 521 | EF685173 | *Caulobacter fusiformis* (97) | Alphaproteobacteria |
| WO15 | 391 | EF685174 | *Sphingomonas aromaticivorans* (97) | Alphaproteobacteria |
| WO16 | 511 | EF685172 | *Brevundimonas vesicularis* (98) | Alphaproteobacteria |
| WO17 | 490 | EF685179 | *Azorhizobium caulinodans* (98) | Alphaproteobacteria |
| WO18 | 434 | EF685168 | *Bacillus thuringiensis* (99) | Firmicutes |

*Isolates coded B are from bamboo leaf infusions, and isolates coded WO are from white oak leaf infusions.

Example 6

Behavioral Bioassay—Response to Odorants from Single Bacterial Isolates

Based on results of experiments involving the mixture of 14 isolates, single isolates were evaluated separately against gravid *Ae. aegypti*. Bacterial cells were diluted to final concentrations of $10^8$, $10^7$, and $10^6$ cells/mL and experiments were set up as described above in Example 3. The 14 bamboo isolates varied in activity with gravid mosquitoes exhibiting significant attraction to some isolates while other isolates were significantly repellant. In binary sticky screen bioassays, significantly more *Ae. aegypti* were trapped in cups that contained cultures of isolate B1 ($10^6$ cells/mL; mean OAI=0.34±0.03; P=0.0001), B5 ($10^8$ cells/mL; mean OAI=0.62±0.07; P+0.0001), B8 ($10^8$ cells/mL; mean OAI=0.036±0.05; P=0.0028), B12 ($10^8$ cells/mL; mean OAI=0.035±0.01; P=0.0001) and B14 ($10^8$ cells/mL; mean OAI=0.38±0.06; P=0.0001). Isolate B5 was the most attractive of the 14 isolates.

Example 7

Figure 3:
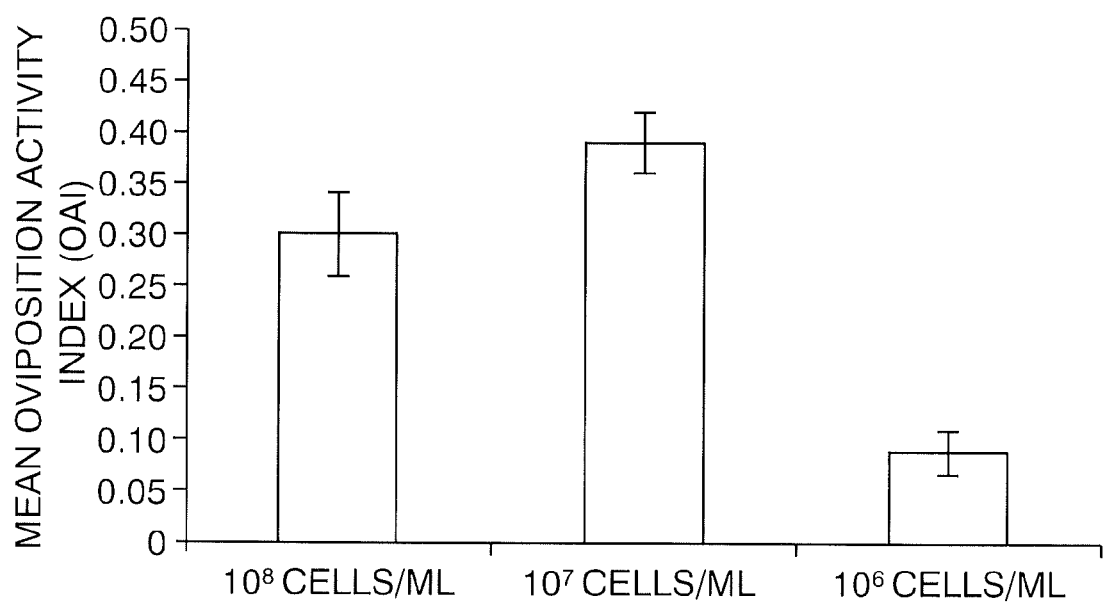
FIG. 3. Attraction of gravid *Ae. aegypti* to a mix of five bacterial isolates in dose-response experiments. Mean OAI values (±SE) are for three trials with six replicate cages for each trial.

Behavioral Bioassays—Response to Odorants from a Mix of Attractive Bacterial Isolates Based on results from single isolate experiments, the 5 bacterial isolates that yielded significant attraction in stage 4 were evaluated further in stage 5 against *Ae. aegypti* and *Ae. albopictus*. Mixtures of the 5 bacterial isolates (B1, B5, B8, B12 and B14) were grown, diluted, and experiments were set up as described above in Example 3. When given a choice between bacterial isolates and control medium, significantly more *Ae. aegypti* were attracted to cups containing all three concentrations of the bacterial tested. A significant proportion of females were attracted to test cups that contained $10^8$ cells/mL (mean OAI=0.30±0.04; P=0.0002) and $10^7$ cells/mL (mean OAI=0.39±0.03; P=0.0005) (FIG. 3).

Figure 4:
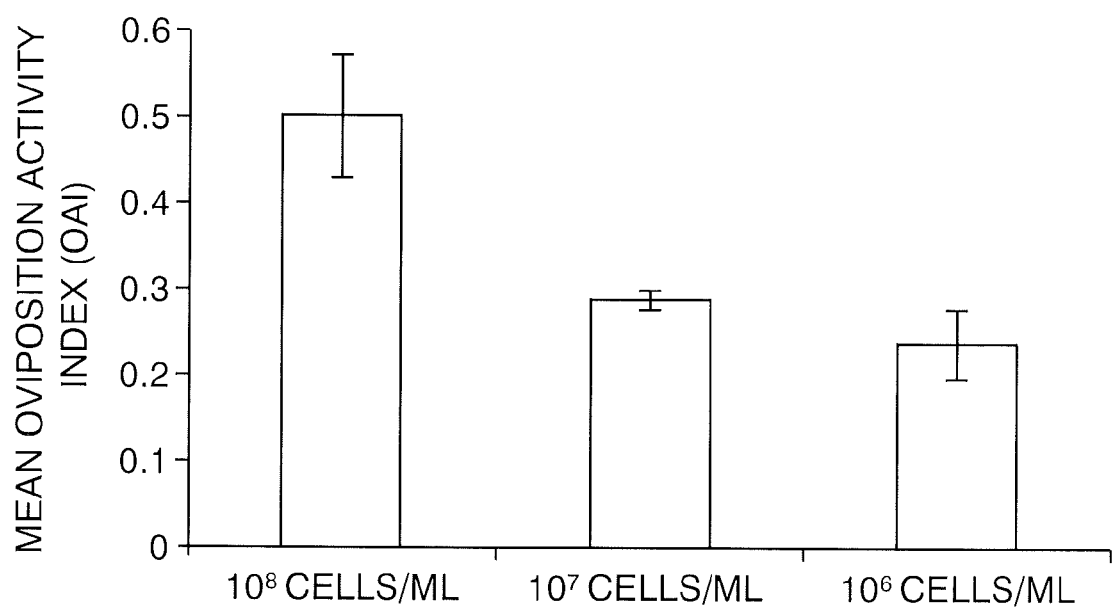
FIG. 4. Attraction of gravid *Ae. albopiectus* to a mix of five bacterial isolates in dose-response experiments. Mean OAI values (±SE) are for three trials with six replicate cages for each trial.

Similarly, when given a choice between a mixture of 5 bacterial isolates and control medium, significantly more gravid *Ae. albopictus* were trapped in cups containing $10^8$ cells to $10^6$ cells than in cups containing control media. The proportion of females attracted to test cups containing $10^8$ cells/mL (mean OAI=0.50±0.13; P=0.0002) and $10^7$ cells/mL (mean OAI=0.29±0.01; P=0.0398) were significantly different from zero (FIG. 4).

Example 8

Behavioral Bioassays—Egg-Laying Response to a Mix of 14 Bacterial Isolates

Figure 5:
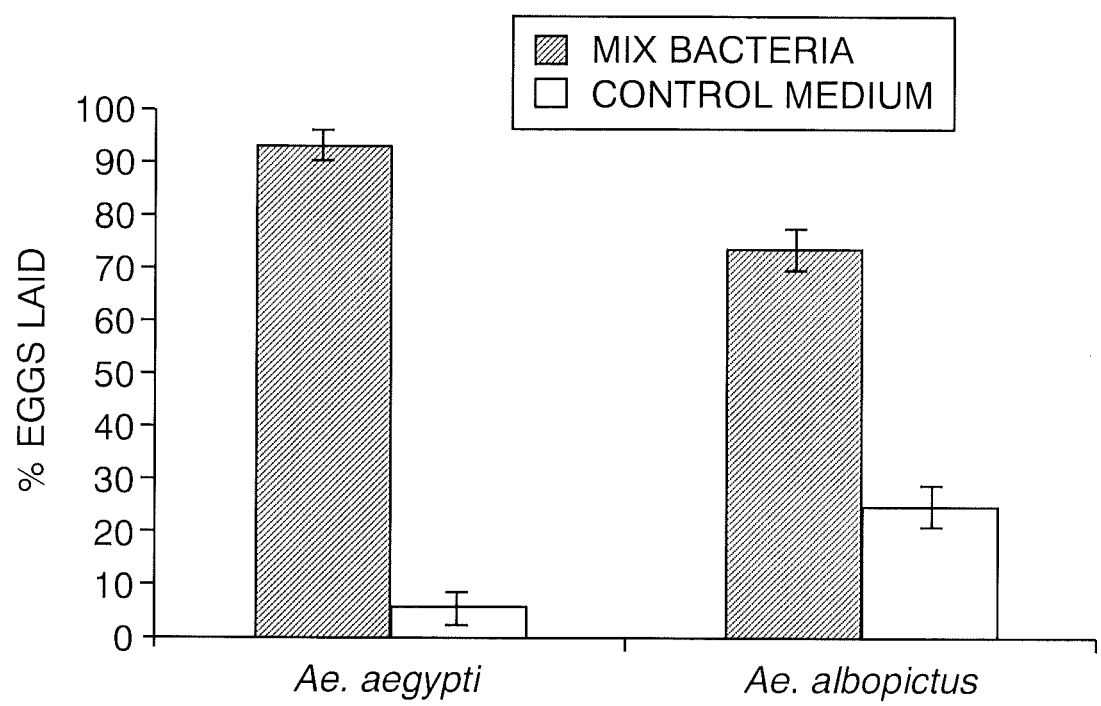
FIG. 5. Egg laying responses of *Ae. aegypti* and *Ae. albopictus* to a mix of 14 different bacterial isolates.

Oviposition responses to a mixture of bacterial isolates mediated by contact chemoreception were evaluated using egg-laying bioassay methods as described in Example 3. Cells grown for 2 days were diluted to a final concentration of $10^8$ cells/mL. It was observed that, *Ae. aegypti* laid a significantly higher percentage of eggs in cups holding test suspensions of the 14 bacterial isolates than in control cups containing R2A medium. The cell density of bacteria ($10^8$ cells/mL) significantly increased the percentage of eggs laid in the test cup versus in the control cup (93.6±10% vs. 6.4%). Similarly, *Ae. albopictus* also laid a significantly higher percentage of eggs in cups containing the 14 bacterial isolates than in cups containing R2A medium (74.6±3.0% vs. 25.4%) (FIG. 5).

Example 9

Behavioral Bioassays—Response to Odorants from a Mixture of Bacterial Isolates

Oviposition responses to different bacterial isolates were evaluated using sticky-screen bioassay methods as described in Example 3. The bacterial isolates were mixed and grown 2 days in R2A medium, and the bacterial cells in these cultures were used in oviposition attractants bioassays as described in Example 3. Bacterial cells were diluted to final concentrations of $10^9$, $10^8$, $10^7$, and $10^6$ cell/mL as determined with a hemocytometer. After dilution to the appropriate cell density, 30 mL of culture was added to the test cup; similarly, control R2A medium was also diluted and added to a control cup. After 24 h of exposure, the numbers of mosquitoes trapped on sticky screens in the test and control cups were counted. When given a choice between mixtures of 14 bacterial isolates and control medium, significantly more *Ae. aegypti* were trapped in the test cups containing bacteria. The number of mosquitoes responding peaked at concentrations of $10^8$ cells/mL (mean Oviposition Activity Index=0.40; P=0.0002) and 107 cells/mL (mean OAI=0.38; P=0.0005), and the mean proportion of mosquitoes responding was significantly different from zero. The OAI represents the proportion of mosquitoes trapped in the cup containing the test material after correcting for the mosquitoes trapped in the control cup.

An additional experiment was similarly done, and gravid females were offered a choice between containers holding fresh sterile medium and culture medium containing a mix of the bacterial species. *Ae. aegypti* laid 93.9±1.5% and 91.1±2.0% of their eggs in cups containing the bacteria from bamboo and white-oak leaf infusions, respectively, and only 6.5% and 9.8% of the total number of eggs in control containers, showing that both sets of bacterial isolates produced highly stimulatory oviposition kairomones. Some individual isolates failed to stimulate egg laying at several cell densities, indicating that only certain bacterial isolates produce the egg-laying cues.

Example 10

Encapsulation of Bacterial in Alginate Beads

A standard alginate encapsulation method was adapted to produce a novel formulation of bacterial species that produce potent mosquito oviposition attractants and stimulants. Cultures of 5 mixed species isolates (see Examples 4 and 5) were grown for 48 h at 28° C. in R2A medium, cells were centrifuged at 1254 g for 10 min, the supernatant was decanted, and cells were suspended in fresh R2A medium that contained sterile 2% sodium alginate. Before beads were made, the bacterial cells were incubated for 2 h on a shaker (150 RPM) at 28° C. to obtain a uniform suspension of bacterial cells in the alginate solution. The alginate-bacteria mixture was expressed as drops through a 30 mL syringe via the luer-lok tip into steril 0.1 $MCaCl_2$, forming beads which were allowed to harden for approximately 10 to 15 min, and then were washed in sterile distilled water.

Example 11

Figure 6:
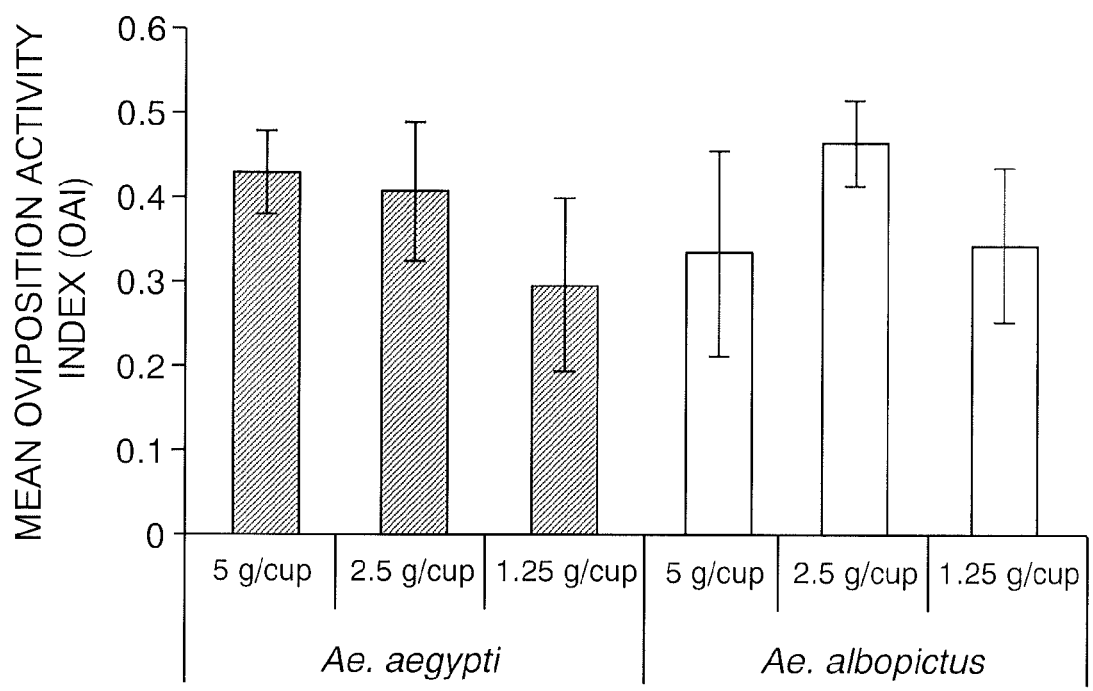
FIG. 6. Attraction of gravid *Ae. aegypti* and *Ae. albopictus* to a mix of five bacterial isolates encapsulated in calcium alginate beads in dose-response experiments. Mean OAI values (±SE) are for three trials with six replicate cages for each trial.

Behavioral Bioassays—Response of Gravid Mosquitoes to a Mix of 5 Attractive Bacterial Isolates Encapsulated in Alginate Beads The encapsulated bacteria (Example 10) were evaluated in the standard binary sticky screen bioassay described (Example 3). Encapsulated bacterial beads were weighed and added at rates of 1.25, 2.5, and 5 g/cup (~25 beads per g) to test cups containing 30 mL of sterile distilled water. Similarly, control beads without bacteria were weighed and added at rates of 1.25, 2.5 and 5 g/cup to control cups. At all three treatment rates, significantly more *Ae. aegypti* were trapped in test cups that contained bacterial beads (FIG. 6). Similar results were obtained for gravid *Ae. albopictus* (FIG. 6). In some embodiments, our invention consists of the calcium alginate encapsulated mix of five bacterial isolates that produce oviposition attractants for *Ae. aegypti* and *Ae. albopictus*.

Example 12

Figure 7:
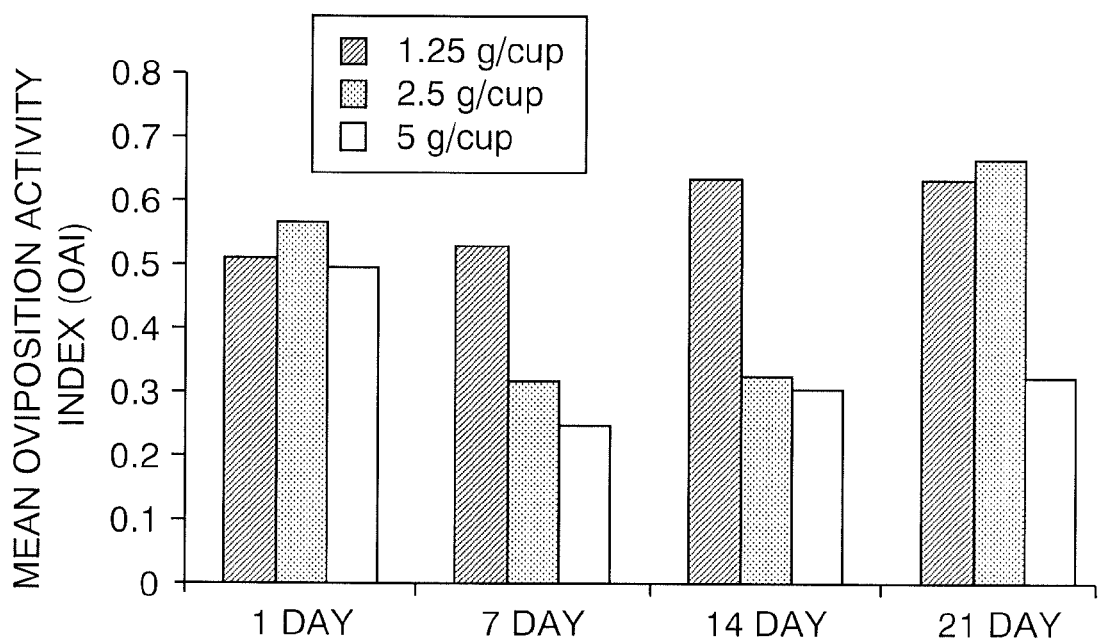
FIG. 7. Attraction of gravid *Ae. aegypti* in dose-response experiments to a mix of five bacterial isolates encapsulated in aged calcium alginate beads. Mean OAI values are for one trial with six replicate cages.

Behavioral Bioassays—Response of Gravid Mosquitoes to Aged Alginate Encapsulated Bacterial Beads Bacteria-encapsulated alginate beads were weighed, added to test cups containing sterile water, and comparable amounts of beads made with sterile R2A medium were added to control cups. Sticky screen behavioral bioassays (Example 3) were conducted 1, 7, 14 and 21 days after beads were added to test cups and sterile R2A medium was added to control cups. At all time points, more *Ae. aegypti* were trapped in test cups that contained 1.25 and 2.5 g of beads per cup than in cups containing 5 g of beads per cup (FIG. 7).

Example 13

Isolation, Identification, and Bioassay of Oviposition Stimulants

Aliquots of 60 mL cultures (109 cells per mL) were centrifuged at 1,254×g for 10 min, the supernatant was decanted, and cells were suspended in 0.6 mL of fresh R2A medium and transferred to 8 mL glass vials. The vials were quick-frozen at −80° C. and lyophilized (Bench Top 6; Virtis; cold trap=−50° C. to −60° C., 200 mTorr, ambient temperature, 23° C.) for 18 h. Vials with dehydrated bacteria were then sealed and stored at −5° C. until needed. Freeze-dried preparations were reconstituted by adding 60 mL of sterile water, and 5 mL of the reconstituted culture suspension was bioassayed immediately in sterile water.

Preliminary bioassays indicated that methanol was more effective than hexane or dichloromethane in extracting the egg-laying kairomones from lyophilized bacteria. The lyophilized bacterial cells in 0.6 mL of R2A medium (equivalent to 60 mL of 109 cells per mL) were extracted with 30 mL of methanol, and the crude extract was centrifuged (1,960×g, 4° C.). The supernatant was rotary evaporated at 40° C. and used in bioassays and chemical analyses. In dose-response studies, 5.0, 0.5, 0.05, and 0.005 mL equivalents of lyophilized bacterial cells were reduced under a gentle stream of $N_2$, and the extract was resuspended in 1.0 mL of ether and aliquoted into eight bioassay cups; control cups received the identical treatment with evaporated methanol resuspended in ether. All cups were aerated in a fume hood for at least 1 h to evaporate ether before bioassays. In dose-response studies, we found that a methanol extract of 0.05 mL equivalents of the bacterial cells (106 cells per mL) was highly stimulatory in binary choice oviposition assays, with 81.6±6.7% of the eggs laid in the extract-treated cup (n=17 assays with single gravid females, P<0.0001).

The methanol extracts were fractionated on a reverse-phase C18 Sep-Pak (Waters) with stepwise elutions of 50%, 75%, 95%, and 100% acetonitrile in water. Each fraction was evaporated in a rotary evaporator to remove acetonitrile and water and redissolved in ether. The 95% acetonitrile fraction was found to be bioactive (78.6±8.7% of the eggs were oviposited in cups containing this fraction; n=17, P<0.0001). The 95% acetonitrile fraction was subjected to two rounds of reverse-phase HPLC (Hewlett Packard 1050) on a Phenomenex Zorbax ODS column (250 mm×4.6 mm, acetonitrile/ water gradient elution: 50-100% acetonitrile in 20 min at 1.0 mL per min, monitored at 265 nm).

For quantitative chemical analysis, 0.6 mL of lyophilized bacterial cells (equivalent to 60 mL of 109 cells per mL) was extracted in 30 mL of methanol. After centrifugation, the supernatant was transferred to a pear-shaped flask, and methanol was rotary evaporated. The residue was suspended in 20 mL of 0.5 M HCl, and the aqueous solution was extracted twice with 10 mL of ether to obtain neutral and acidic compounds. Acidic compounds were extracted from the combined ether layer with 20 mL of 0.5 M NaOH. Then, the alkaline aqueous layer was acidified with 5 M HCl and extracted twice with 10 mL of ether to recover the acidic compounds. The ether layer was washed with brine until the pH became neutral and dried over anhydrous $Na_2SO_4$. An aliquot of the obtained acidic fraction was reacted with trimethylsilyl diazomethane to derivatize fatty acids to the corresponding methyl esters. The ether layer, from which acidic compounds had been extracted, and which contained neutral compounds, including esters, was washed with brine until the pH became neutral, and dried over anhydrous $Na_2SO_4$. An aliquot of the neutral fraction was subjected to GC-MS analysis in SIM mode (m/z 74 and molecular masses of target compounds).

GC-MS analysis was conducted on an Agilent 5975 mass selective detector, operated in electron-impact ionization mode and coupled to an Agilent 6890 GC. The GC was operated in splitless injection mode and fitted with a 30 m×0.25 mm×0.25 μm DB-5MS column programmed from 40° C. to 250° C. at 10° C. per min after an initial delay of 2 min, and held at 250° C. for 20 min. Injector, MSquad, MSsource, and transfer line temperatures were 280° C., 150° C., 230° C., and 250° C., respectively. Mass spectra were compared to Wiley7/NIST05 mass spectra libraries. GC-MS analysis of a 1-mL RP-HPLC fraction that contained bioactive compounds [76.8 vs. 23.2% (SE=7.5), t=3.110, df=17, P=0.0032] revealed a mix of carboxylic acids ranging from nonanoic acid to octadecanoic acid and several carboxylic acid methyl esters, which are listed in Table 2.

TABLE 2

Carboxylic acids and methyl esters identified from a bioactive 1-min (1 mL) HPLC fraction of a methanol extract of lyophilized bacterial cells and quantified from the crude methanol extract

| Compound | Amount (±SEM) extrapolated to 0.05-ml equivalents of the culture medium ($10^6$ cells per ml), ng* | Ratio (% of total) of eight compounds | Ratio (% of total) of three bioactive compounds |
|---|---|---|---|
| Nonanoic acid | 0.027 (0.013) | 0.78 | 15.94 |
| Decanoic acid | 0.013 (0.006) | 0.38 | |
| Dodecanoic acid | 0.111 (0.076) | 3.20 | |
| Tetradecanoic acid | 0.142 (0.021) | 4.08 | 83.01 |
| Tetradecanoic acid, methyl ester | 0.002 (0.001) | 0.05 | 1.05 |
| Hexadecanoic acid | 2.640 (0.756) | 75.77 | |
| Hexadecanoic acid, methyl ester | 0.024 (0.010) | 0.68 | |
| Octadecanoic acid | 0.524 (0.412) | 15.05 | |

Amount (in nanograms) corrected per 0.05-ml equivalents of the bacterial culture ($10^6$ cells per ml), which were highly stimulatory in binary choice oviposition assays (81.6 ± 6.7% of the eggs placed in the extract-treated cup; n = 17 assays with single gravid females, P < 0.0001).
*For chemical analysis, 0.6 ml of lyophilized bacterial cells (equivalent to 60 ml of $10^9$ cells per ml) was extracted in 30 ml of methanol and processed for GC-MS analysis, n = 4.

Acid-base partitioning of this fraction showed that the acid fraction contained oviposition kairomones, whereas the basic fraction, which also contained neutral compounds, was deterrent (Table 3).

TABLE 3

Oviposition-stimulatory activity of a RP-HPLC fraction and its acidic and basic constituents

| Fraction* | No. of assays† | Treatment, % | Control, % | SEM, % | Eggs per Assay ± SEM | t | p‡ |
|---|---|---|---|---|---|---|---|
| 1-min HPLC fraction | 21 | 66.8 | 33.2 | 8.0 | 75.9 ± 4.8 | 2.357 | 0.0143 |
| Basified fraction | 22 | 38.2 | 61.8 | 7.3 | 84.0 ± 4.7 | −1.448 | 0.0811 |
| Acidified fraction | 23 | 74.3 | 25.7 | 7.7 | 78.4 ± 6.3 | 2.970 | 0.0035 |

*A 0.05-ml equivalent of culture was used in each bioassay.
†Twenty-four single female assays were conducted for each treatment. Assays in which a female oviposited <20 eggs in total in 72 h were discarded.
‡Based on paired t test of arcsin√x transformed data, using a one-tailed test. Bold numbers indicate significant stimulation of oviposition.

Synthetic Compounds

Methyl esters were derivatized as follows: A sample in 100 μL of ether, which was equivalent to 3 mL of bacterial culture, was placed in a conical vial, the ether was evaporated with a $N_2$ stream, and 1 μg of hendecanoic acid (internal standard) was added in 20 μL of hexane, followed by 5 μL of methanol and 5 μL of 2.3% diazomethane in hexane. The reaction mixture was stirred vigorously and incubated at room temperature for 30 min. The reaction mixture was diluted 10-fold and 1 μL of the diluted sample was injected into the GC-MS in SIM mode. The undiluted reaction mixture was also subjected to GC-MS analysis in SCAN mode for qualitative analysis.

Synthetic compounds were bioassayed by placing hexane solutions on the surface of sterile distilled water; water in control cups was treated with hexane alone. The hexane was evaporated in a fume hood before bioassays commenced. Each bioassay was with a single female and lasted 72 h.

repeated these assays using five females in 24 h assays. Under these conditions, 1 ng of tetradecanoic acid was highly stimulatory, with a clear decline in the oviposition responses at both lower and higher doses (Table 5), and each of the five females averaged 43.4±3.9 eggs in 24 h.

TABLE 4

Egg-laying bioassays of *Ae. aegypti*, showing dose-response patterns to synthetic carboxylic acids and methyl esters identified from a 1-min (1 mL) HPLC fraction of a methanol extract of lyophilized bacterial cells

| Tested Compound | Dose, ng | n assays* | Treatment, % | Control, % | SEM, % | Eggs per assay | t | p† |
|---|---|---|---|---|---|---|---|---|
| Nonanoic acid | 1 | 22 | 38.6 | 61.4 | 8.4 | 70.9 ± 4.0 | −1.3612 | 0.0939 |
|  | 10 | 22 | 58.3 | 41.7 | 7.7 | 74.3 ± 6.1 | 0.9928 | 0.1661 |
|  | 100 | 20 | 69.1 | 30.9 | 7.3 | 80.0 ± 3.3 | 2.3936 | 0.0136 |
| Decanoic acid | 1 | 18 | 43.7 | 56.3 | 8.6 | 60.0 ± 5.6 | −0.9281 | 0.1832 |
|  | 10 | 19 | 52.2 | 47.9 | 9.5 | 61.3 ± 5.0 | 0.2907 | 0.3873 |
|  | 100 | 13 | 45.8 | 54.2 | 11.3 | 67.0 ± 7.0 | −0.6707 | 0.2576 |
| Dodecanoic acid | 1 | 22 | 47.0 | 53.1 | 8.8 | 67.3 ± 4.0 | −0.1725 | 0.4324 |
|  | 10 | 20 | 43.4 | 56.6 | 9.9 | 66.3 ± 3.1 | −0.6563 | 0.2598 |
|  | 100 | 20 | 47.6 | 52.4 | 8.8 | 63.8 ± 3.4 | −0.4214 | 0.3389 |
|  | 0.01 mg | 26 | 52.2 | 47.8 | 7.9 | 66.5 ± 4.2 | 0.4157 | 0.3406 |
|  | 0.1 mg | 28 | 45.8 | 54.3 | 7.7 | 64.4 ± 2.9 | −0.6835 | 0.2501 |
|  | 1.0 mg | 28 | 42.2 | 58.8 | 8.6 | 60.2 ± 2.8 | −1.0455 | 0.1525 |
| Tetradecanoic acid | 1 | 24 | 45.4 | 54.6 | 8.2 | 79.6 ± 2.7 | −0.5287 | 0.3010 |
|  | 10 | 23 | 81.0 | 19.0 | 6.9 | 87.7 ± 5.1 | 4.6939 | 0.0001 |
|  | 100 | 23 | 62.1 | 37.9 | 8.3 | 80.2 ± 5.2 | 1.3952 | 0.0884 |
| Tetradecanoic acid, methyl ester | 1 | 21 | 55.0 | 45.0 | 9.5 | 68.3 ± 5.4 | 0.5160 | 0.3058 |
|  | 10 | 19 | 70.2 | 29.8 | 8.4 | 64.0 ± 7.1 | 2.1661 | 0.0220 |
|  | 100 | 19 | 51.0 | 49.0 | 8.9 | 70.6 ± 6.0 | −0.0185 | 0.4927 |
| Hexadecanoic acid | 1 | 21 | 53.4 | 46.6 | 8.9 | 63.7 ± 4.2 | 0.1818 | 0.4288 |
|  | 10 | 17 | 43.2 | 56.8 | 8.0 | 63.5 ± 4.9 | −0.9320 | 0.1826 |
|  | 100 | 19 | 38.2 | 61.8 | 9.4 | 71.8 ± 4.8 | −1.1175 | 0.1392 |
| Hexadecanoic acid, methyl ester | 1 | 19 | 34.7 | 65.4 | 8.3 | 51.0 ± 3.5 | −1.8761 | 0.0385 |
|  | 10 | 18 | 59.1 | 40.9 | 9.0 | 51.3 ± 3.0 | 0.7242 | 0.2394 |
|  | 100 | 17 | 60.4 | 39.6 | 10.1 | 58.6 ± 3.8 | 0.9887 | 0.1688 |
| Octadecanoic acid | 1 | 19 | 55.1 | 44.9 | 9.0 | 71.3 ± 3.3 | 0.5397 | 0.2980 |
|  | 10 | 20 | 46.4 | 53.7 | 9.7 | 69.0 ± 3.6 | −0.4201 | 0.3395 |
|  | 100 | 19 | 58.4 | 41.6 | 8.4 | 64.8 ± 4.8 | 0.9383 | 0.1802 |

*Twenty-four assays were conducted for each compound-dose combination with individual gravid females. Assays in which a female oviposited <20 eggs in total in 72 h were discarded; on average, 19.75 ± 0.48 of the 24 assays were included.
†Based on paired t test of arcsin√x transformed data, using a one-tailed test. Bold numbers indicate significant stimulation of oviposition.

TABLE 5

Egg-laying bioassays of *Ae. aegypti*, showing dose-response patterns to tetradecanoic acid, using five females per assay in 24-h assays

| Dose, ng | No. of assays | Treatment, % | Control, % | SEM, % | Eggs per Assay | t | p* |
|---|---|---|---|---|---|---|---|
| 0.01 | 12 | 52.3 | 47.7 | 4.7 | 318.5 ± 14.4 | 0.469 | 0.3240 |
| 0.1 | 12 | 57.8 | 42.2 | 6.4 | 232.1 ± 22.3 | 1.239 | 0.1206 |
| 1.0 | 12 | 76.9 | 23.1 | 8.6 | 216.8 ± 19.4 | 5.935 | <0.0001 |
| 10 | 12 | 57.9 | 42.1 | 6.8 | 196.4 ± 23.2 | 1.202 | 0.1274 |
| 100 | 12 | 38.7 | 61.3 | 8.4 | 260.4 ± 30.9 | −1.254 | 0.1179 |

*Based on paired t test of arcsin√x transformed data, using a one-tailed test. Bold numbers indicate significant stimulation of oviposition.

Figure 8:
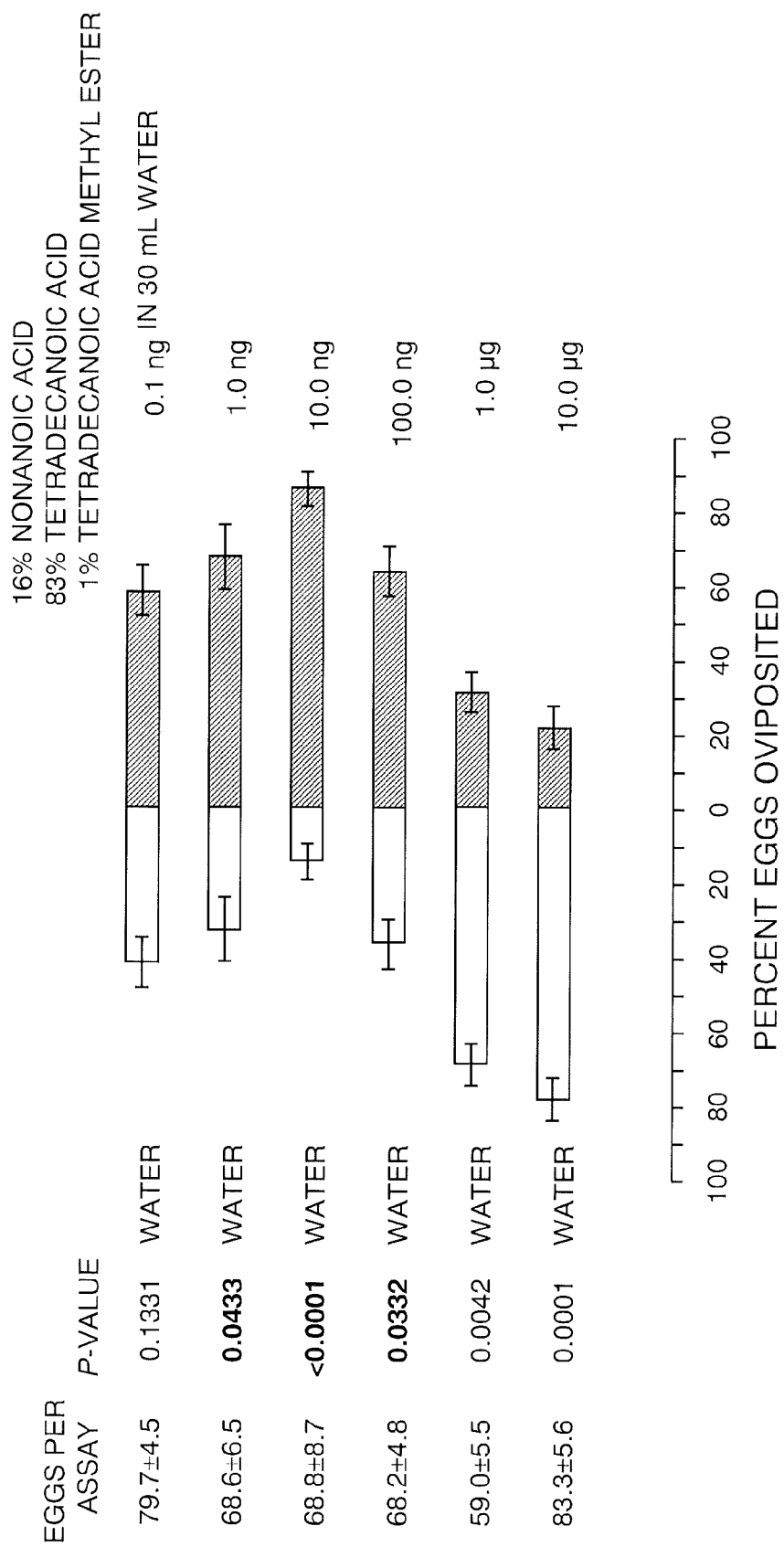
FIG. 8. Egg laying responses of *Ae. aegypti*, showing dose-response patterns to blends of two bioactive carboxylic acids and a methyl ester.

Synthetic compounds and blends were bioassayed at 1, 10, and 100 ng in cups filled with 30 mL of water (0.14, 1.46, and 14.6 nM for tetradecanoic acid). Most fatty acids and esters were ineffective at any concentration (Table 4). However, others, namely nonanoic acid, tetradecanoic acid, and methyl tetradecanoate, were highly effective at inducing egg laying but at extremely narrow dosage ranges. Tetradecanoic acid, at 10 ng, diverted the greatest amount of oviposition to the treated water. These assays, using single females, were conducted for 72 h, and females laid 22.6±0.6 eggs per 24 h, on average, whereas in previous 24 h assays with five females, each female deposited 43.3±3.4 eggs. To confirm that these compounds were effective in assays of shorter duration, we A blend of synthetic carboxylic acids at their natural ratio in bacteria, as determined from GC-MS analysis of methanol extracts of a lyophilized bacterial mix that was highly stimulatory in oviposition assays (FIG. 1, experiment 9), were also assayed. A blend of bioactive compounds, consisting of 16% nonanoic acid, 83% tetradecanoic acid, and 1% methyl tetradecanoate (Table 3) was highly stimulatory to *Ae. aegypti* females. A curvilinear response was observed, with the highest percentage of eggs (85.5±11%) laid in cups containing 10 ng of the blend (FIG. 8). Notably, blending the three bioactive compounds in their natural ratio did not synergize the activity of the blend beyond what was observed for tetradecanoic acid alone. However, the dose-response curve to the blend of three components spanned over two log scales (1-100 ng, with tetradecanoic acid at 0.12-12.12 nM), whereas the oviposition response to individual components was limited to narrow dosage ranges. Results suggested that gravid *Ae. aegypti* perceive specific carboxylic acids and esters associated with microorganisms in their oviposition habitat, and these kairomones radically alter their oviposition decisions. Although some bacteria-associated cues may induce oviposition at specific concentrations, the same cues at higher concentrations (e.g., tetradecanoic acid), or other cues produced by either the same or different bacteria (e.g., hexadecanoic acid methyl ester), may deter oviposition.

The foregoing is illustrative of the present invention, and is not to be construed as limiting thereof. The invention is defined by the following claims, with equivalents of the claims to be included therein.

What is claimed is:

1. A method of attracting a mosquito to a target, the method comprising applying to the target a mosquito attractant composition comprising one or more of: *Lactococcus* lactic; *Klebsiella oxytoca*; *Shigella dysenteriae*; *Brevundimonas vesicularis*; a supernatant of a culture of any of the aforementioned bacteria; or any combination thereof, in an amount effective in the mosquito attractant composition to attract the mosquito to the target, wherein the mosquito attractant composition is in the form of a liquid, pellet, particle, tablet, or bead.

2. The method of claim 1, wherein the composition comprises the supernatant.

3. The method of claim 1, wherein the mosquito is an *Aedes* mosquito.

4. The method of claim 1, wherein the mosquito is *Aedes aegypti*, *Aedes albopictus*, or a combination thereof.

5. The method of claim 1, wherein the mosquito is gravid.

6. The method of claim 1, wherein the composition comprises two or more of: *Lactococcus lactis, Klebsiella oxytoca, Shigella dysenteriae, Brevundimonas vesicularis*, or a bacterial culture supernatant thereof.

7. The method of claim 1, wherein the composition stimulates oviposition.

8. The method of claim 1, wherein the composition comprises *Lactococcus lactis* or a bacterial culture supernatant thereof.

9. The method of claim 1, wherein the composition comprises *Klebsiella oxytoca* or a bacterial culture supernatant thereof.

10. The method of claim 1, wherein the composition comprises *Shigella dysenteriae* or a bacterial culture supernatant thereof.

11. The method of claim 1, wherein the composition comprises *Brevundimonas vesicularis* or a bacterial culture supernatant thereof.

12. A mosquito trap comprising:
a) a trapping chamber or adhesive; and
b) a mosquito attractant composition positioned to attract a mosquito, wherein the mosquito attractant composition comprises a suitable carrier and one or more of: *Lactococcus lactis; Klebsiella oxytoca; Shigella dysenteriae; Brevundimonas vesicularis*; a supernatant of a culture of any of the aforementioned bacteria; or any combination thereof, in an amount effective in the mosquito attractant composition to attract the mosquito to the mosquito trap.

13. The mosquito trap of claim 12, wherein the composition comprises the supernatant.

14. The mosquito trap of claim 12, wherein the mosquito is an *Aedes* mosquito.

15. The mosquito trap of claim 12, wherein the mosquito is *Aedes aegypti*, *Aedes albopictus*, or a combination thereof.

16. The mosquito trap of claim 12, wherein the mosquito is gravid.

17. The mosquito trap of claim 12, wherein the composition comprises two or more of: *Lactococcus lactis, Klebsiella oxytoca, Shigella dysenteriae, Brevundimonas vesicularis*, or a bacterial culture supernatant thereof.

18. The mosquito trap of claim 12, wherein the composition stimulates oviposition.

19. The mosquito trap of claim 12, wherein the composition comprises *Lactococcus lactis* or a bacterial culture supernatant thereof.

20. The mosquito trap of claim 12, wherein the composition comprises *Klebsiella oxytoca* or a bacterial culture supernatant thereof.

21. The mosquito trap of claim 12, wherein the composition comprises *Shigella dysenteriae* or a bacterial culture supernatant thereof.

22. The mosquito trap of claim 12, wherein the composition comprises *Brevundimonas vesicularis* or a bacterial culture supernatant thereof.

* * * * *